United States Patent [19]

Portnuff et al.

[11] Patent Number: 5,284,152

[45] Date of Patent: Feb. 8, 1994

[54] METHOD FOR DISPLAYING SUPERIMPOSED HEARTBEAT WAVEFORMS

[75] Inventors: Colin M. Portnuff, Tualatin; Matthew S. Glei; Rommel R. Raj, both of McMinnville, all of Oreg.

[73] Assignee: Hewlett-Packard Company, Palo Alto, Calif.

[21] Appl. No.: 843,368

[22] Filed: Feb. 28, 1992

[51] Int. Cl.$^5$ .......................................... A61B 5/0402
[52] U.S. Cl. ................................................. 128/710
[58] Field of Search .................. 128/710, 712, 696; 364/413.06

[56] References Cited

U.S. PATENT DOCUMENTS 4,537,202  8/1985  Mancini et al. .................. 128/712
4,721,114  1/1988  DuFault et al. .................. 128/696
4,896,677  1/1990  Kaneko et al. ................... 128/696

Primary Examiner—William E. Kamm
Assistant Examiner—Scott M. Getzow

[57] ABSTRACT

A computer controls a video display having a display screen for displaying ECG heartbeats superimposed over one another. The ECG data is collected during Holter monitoring and stored in a memory. A plurality of successive heartbeats are written to the display with their R-waves aligned. As the next new heartbeat in chronological order is displayed the longest-displayed heartbeat is removed. The total number of heartbeats displayed therefore remains constant. The user can select the total number of heartbeats, between one and five, to be displayed at one time. In one mode, a heartbeat is added, and removed, during each screen refresh cycle. In another mode, the user can step the display in either reverse or forward chronological order one step at a time.

6 Claims, 9 Drawing Sheets

TIME=t

TIME=t+1

TIME=t+2

TIME=t+3

METHOD FOR DISPLAYING SUPERIMPOSED HEARTBEAT WAVEFORMS

BACKGROUND OF THE INVENTION

1. Field of the Invention

The present invention relates generally to methods and apparatus for displaying ECG waveforms and more particularly to such methods and apparatus in which heartbeat waveforms contained in stored ECG data are displayed superimposed over one another.

2. Description of the Related Art

In a Holter ECG monitoring system, a patient is fitted with a monitor which detects and stores continuous ECG waveforms. Sometimes several electrodes are connected to the patient so that two or more channels are recorded. It is not unusual for such a monitor to be worn for many hours thereby generating thousands of periodic heartbeat waveforms which are stored for later review to assist in diagnosis and treatment of the patient.

Sometimes such waveforms are displayed by superimposing a predetermined number of heartbeats on a screen in rapid succession. Each time a new heartbeat appears on the screen, the longest-displayed heartbeat is removed from the screen. Such a display allows a clinician to see beat-to-beat changes in the patient's ECG complex which may be significant. Holter monitors can produce as many as 100,000 consecutive beats which must be analyzed to identify both short-term and long-term changes. When an abnormal complex is displayed, the user is interested in the shape and quantity of abnormal complexes, especially when seen in close proximity to each other. Multiple sequential abnormal complexes are of special importance; the superimposition display is provided to detect such sequences.

Early forms of the superimposition display scanned each beat once on a high persistence phosphor in a cathode ray tube (CRT). The CRT displayed, albeit on a gradually dimming basis, several of the heartbeats at once. Thus, a user was able to observe an integer number of heartbeats where the number of heartbeats observed was determined by the phosphor characteristics of the CRT. More recent systems have been developed which use digital memory to store and display the beats of interest. Some such systems display one beat at a time and rely upon an observer's eye to integrate several successive beats during the search for abnormal complexes and runs thereof.

Some digital systems now provide for a fixed number of beats to be overlaid and displayed simultaneously. One such system displays 12 beats. When a new beat is added to the display, the oldest beat is removed. Sequential new beats are periodically added (and old beats removed) one at a time, to facilitate rapid review of the data. This prior art approach is disadvantageous in that a user cannot easily differentiate between short and long continuous runs of ectopy, or other abnormalities, nor can a user select a threshold to optimize searching for a predetermined number of sequential abnormal complexes.

Another method for displaying stored ECG data is to display a continuous static ECG waveform. Typically the waveform is presented from left to right across the screen in a plurality of rows. A user can page forward or backward through the stored data to display different portions of the waveform on the display screen. Such a display optimizes the ability of a clinician to detect patterns of abnormal heartbeats, such as bigeminy, as well as rate information which is derived from the spacing of each heartbeat waveform.

Thus, the superimposition display provides excellent beat-by-beat detail for the displayed beats but larger patterns of beats, as well as rate information, are lost. In one prior art superimposition display system, some rate information is provided in a superimposition display screen. As each new beat is superimposed on the screen, a horizontal line is drawn on the screen to one side of the waveform display. Each horizontal line is proportional in length to the interval between R-waves of the currently displayed heartbeat waveform and the immediately preceding one. A rough plot of rate information is thus also available to the clinician in association with the superimposition display. The remainder of the waveform data, including any heartbeat waveform patterns which develop, is not presented by this prior art system.

SUMMARY OF THE INVENTION

A method for displaying stored ECG data representative of a plurality of heartbeats. A continuous ECG waveform derived from the stored data is painted on a first display. Each heartbeat painted on the first display is superimposed on a second display.

Apparatus constructed in accordance with the present invention is also provided.

The present invention is advantageous in that it provides associated displays of a continuous ECG waveform, which provides rate and pattern information, and a superimposition display, which provides information relating to abnormal ECG complexes and sequential runs of abnormal complexes.

DETAILED DESCRIPTION OF THE PREFERRED EMBODIMENT

Figure 1:
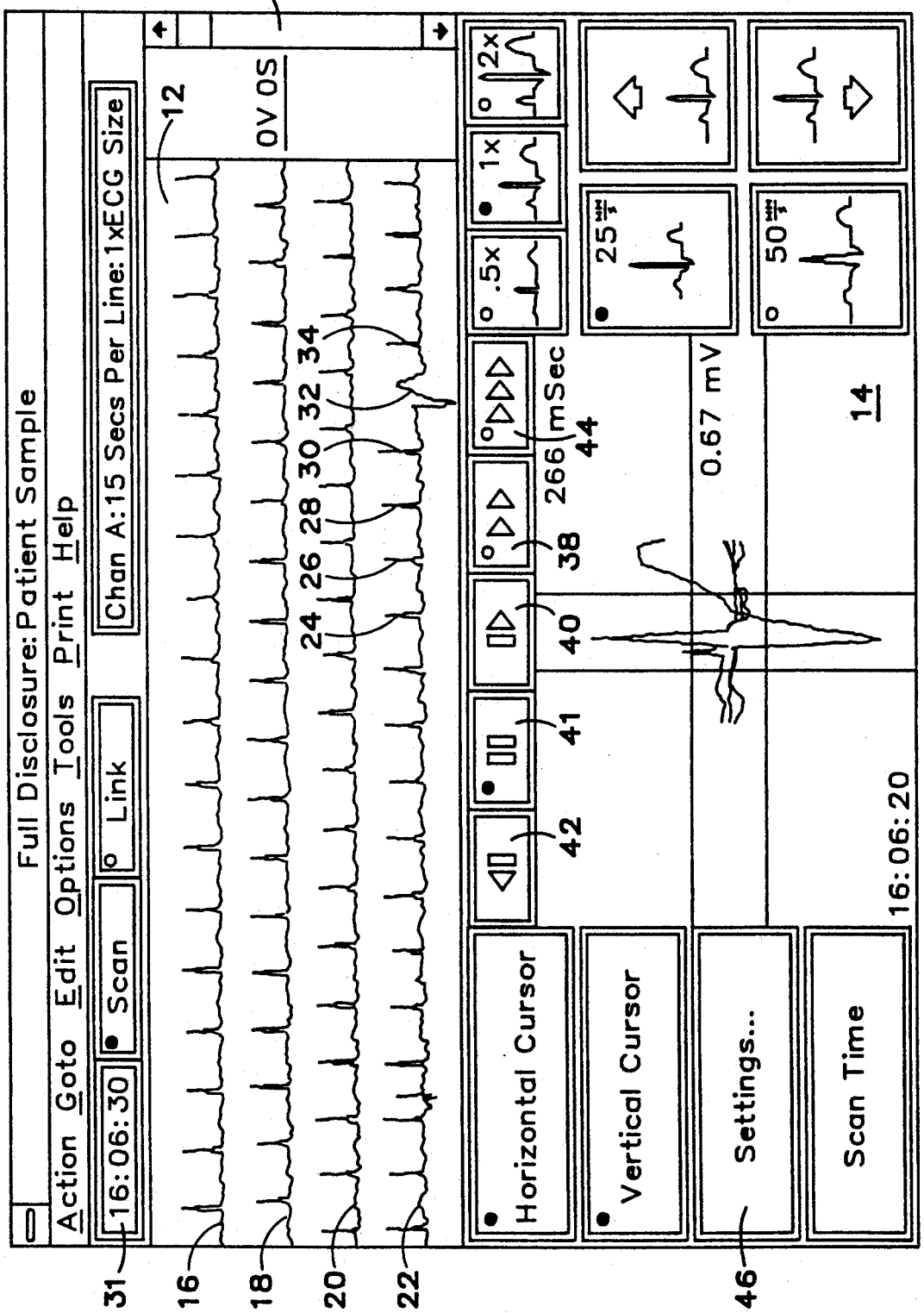
FIG. 1 is a view of a CRT screen upon which stored ECG data is displayed pursuant to the present invention.

Turning now to FIG. 1, indicated generally at 10, is a display formed on a CRT screen incorporated into a system constructed in accordance with the present invention. The present embodiment of the invention comprises a personal computer having an Intel TM 386 processor, a keyboard, a color VGA monitor, a mouse, and a Microsoft Windows TM graphical user interface. The computer is programmed, in a manner which is described in more detail hereinafter, to operate in accordance with the following description of the preferred embodiment.

Prior to describing the manner in which the computer program, represented by the chart of FIG. 7, controls the system, description will first be made of the user interface and of the manner in which the present embodiment is used to display heartbeat waveforms contained in stored ECG data.

The stored ECG data to be analyzed is collected by a Holter monitor which is fitted to a patient for detecting and storing a continuous ECG waveforms for many hours. Often, two vector are used so that the monitor stores two simultaneously-generated continuous ECG waveforms. Some such monitors are equipped with processors for performing automated preliminary analysis of the ECG waveforms as they are stored. For example, each heartbeat waveform is assigned to a morphology classification, such as ventricular ectopic beat, dominant beat, pace beat, artifact, etc. In addition, a heartbeat waveform which is representative of all the heartbeat waveforms in each morphology is identified. The total number of heartbeat waveforms in each morphology is also computed. A peak detector algorithm locates the R-wave of each heartbeat waveform. An analysis is made of the shape of each waveform to assign a time of occurrence within millisecond resolution to each R-wave. The time of occurrence is referenced to a twenty-four hour clock which keeps the time of day. The continuous ECG waveform, comprised of a plurality of individual heartbeat waveforms, is stored in chronological order. After a predetermined amount of data is collected in the Holter monitor, it is removed from the patient and connected to the system of the present invention in a known manner for transferring the ECG waveforms, in the case where two leads are attached, as well as the information generated by the preliminary analysis performed by the monitor processor, to the system computer.

Indicating generally at 10 in FIG. 1 is a CRT display screen upon which stored ECG waveforms are represented in accordance with the present invention. The waveforms on screen 10 were generated by a patient as described above. The collected data along with the information generated by the preliminary analysis performed by the Holter monitor is transferred to the system in which screen 10 is incorporated.

Display screen 10 includes a first display 12 and a second display or scan window 14. The continuous ECG waveform is displayed on rows 16, 18, 20, 22 on screen 12. The waveform on screen 12 is displayed in chronological order with the right-most end of row 16 continuing at the left-most end of row 18 and the right-most end of row 18 continuing on row 20, and so forth. The waveform on display 12 is stationary in the present mode of operation of the system.

The continuous ECG waveform on display 12 is made up of a plurality of successive heartbeat waveforms, like heartbeat waveforms 24, 26, 28, 30, 32, 34. Each of these pulses is known in the field of cardiology as a QRS. The heartbeat waveforms are also referred to herein simply as heartbeats. The normal heartbeat waveforms, and some abnormal waveforms, are characterized by a vertical pulse having an upper tip which comprises the maximum amplitude of each heartbeat waveform. This pulse is referred to herein as an R-wave.

A scroll bar 29 enables a user to display different portions of the stored continuous ECG waveforms on display 12 by scrolling through the data in a known manner. A time display 31 indicates the chronological position of the rows displayed on screen 12 relative to the entire stored waveform with 16:06:30 being the time of day in hours, minutes and seconds when the beginning of the waveform on display 12 was recorded.

Scan window 14 includes five consecutive heartbeat waveforms from the stored ECG data superimposed over one another as shown. All of the heartbeats in window 14 are aligned at the peaks of their respective R-waves.

The various buttons surrounding display 14 control the manner in which heartbeat waveforms are displayed thereon. Each button is actuated by using a mouse (not shown) to position a cursor (also not shown) on CRT screen 10 over the button to be actuated. When the cursor is so positioned, the mouse is clicked, thus actuating the button. It can be seen that several of the buttons have a circle in the upper left hand corner thereof. Some buttons change mode of operation of display 14 until the button is again actuated. When such buttons are actuated as described above, the circle fills when the button is actuated and remains filled until the button is again actuated. When the circle is filled, the mode of operation controlled by the button is referred to herein as being selected. It is to be appreciated that the buttons are not mechanical buttons but rather are images formed on CRT screen 10 in a known manner. Creation of such buttons which are actuatable as described above may be implemented by a person having ordinary skill in the art.

Display screen 14 includes 5 consecutive heartbeat waveforms, taken from the stored ECG data, superimposed over one another with their R-waves aligned. In the present embodiment of the invention, the display on CRT 10 is controlled by a VGA graphics board which causes the CRT to be refreshed, i.e., written upon, 60 times per second. A forward button 38, when selected, causes the longest-displayed heartbeat to be removed and the next heartbeat to be displayed each time the CRT is refreshed. Thus, 5 heartbeats are always displayed on window 14. For example, assume window 14 currently displays heartbeat waveforms 24, 26, 28, 30, 32. During the next screen refresh cycle, waveform 24 is removed and window 14 displays heartbeats 26, 28, 30, 32, 34. During the next screen refresh cycle waveform 26 is removed and the next waveform in chronological order, to the right of waveform of 34, is added to the display. It should noted that while display 14 changes as described, in this mode of operation, the waveform on display 12 remains fixed as shown in FIG. 1 even when the scanning in display 14 proceeds to heartbeat waveforms later in time than any of those seen on display 12. The R-wave time from the most recently displayed heartbeat appearing on display 14, in hours, minutes and seconds, appears at the lower left of display 14.

Description will now be made of additional buttons surrounding display 14 and the manner in which they control scanning of heartbeat waveforms on display 14. Actuation of a stop button 41 stops automatic scanning when, e.g., forward button 38 is selected. When stop button 41 is selected, the display continues to display superimposed heartbeats, but does not change. A single-beat forward button 40 permits an operator to scan heartbeat waveforms in display 14 as described above except that a new heartbeat is added, and the oldest-displayed heartbeat is removed, only upon actuation of button 40. Thus, an operator can carefully examine each new group of superimposed heartbeat waveforms on display 14. Actuation of button 40 is referred to herein as an operator signal.

Similarly, a single-beat reverse button 42 permits an operator to reverse the direction of scanning. In other words, when button 42 is first actuated, the heartbeat which was most recently-removed from display 14 is added back to the display and the shortest-displayed heartbeat is removed from the display. For example, assume display 14 contains heartbeats 26, 28, 30, 32, 34 superimposed. When button 41 is actuated, scanning stops. Upon actuation of button 42, heartbeat 34 disappears from the display and heartbeat 24 added. If button 42 is again actuated, heartbeat 32 disappears and the beat to the left of heartbeat 24 in display 12 is added, and so forth. Thus, when button 38 is actuated, scanning occurs automatically at a relatively rapid rate in increasing chronological order of the continuous ECG waveform. If an operator observes a pattern of interest, button 41 is actuated to stop the display. Thereafter, the display is adjusted one beat at a time, using buttons 40, 42, to locate and display the beat or beats of interest where they can be studied at length so long as button 41 remains selected.

Fast-forward button 44 causes display 14 to display a preselected number of consecutive beats at a time and, in the next refresh cycle, display the next-adjacent preselected number of beats and so forth. In this mode, each beat is displayed only once. For example, if the system is set (in a manner which will be later explained) to display two beats at a time when fast-forward button 44 is selected, beats 24, 26 are displayed superimposed, and in the next refresh cycle, beats 28, 30 are displayed superimposed and thereafter beats 32, 34 and so forth. This permits an operator to scan more rapidly through the ECG heartbeats than when forward button 38 is selected.

The buttons in the lower right corner of CRT screen 10 permit an operator to adjust the vertical and horizontal scales of display 14 and to raise and lower the waveform baseline.

The cursor buttons to the left of display 14 cause horizontal and vertical lines as shown to appear on the display when the appropriate button is selected. These lines provide a reference for evaluating beat-to-beat changes in waveform shape and magnitude. The reference lines can be moved to any position in the scan window. The measurements displayed in the window, 266 mSec and 0.67 mV, indicate the distance between the vertical and horizontal lines in milliseconds and millivolts, respectively.

The lower left Scan Time button causes a panel (not shown) to appear on screen 10 which includes a window in which a preselected time can be entered and a scroll bar for scrolling in time. This permits a user to select a time between the beginning and end of the continuous ECG waveform either by typing the time at the computer keyboard or by scrolling. Once a time is so selected, heartbeats immediately adjacent to selected time appear superimposed in display 14. Forward or reverse scanning as described above then commences from the new location on the continuous ECG waveform.

Figure 2:
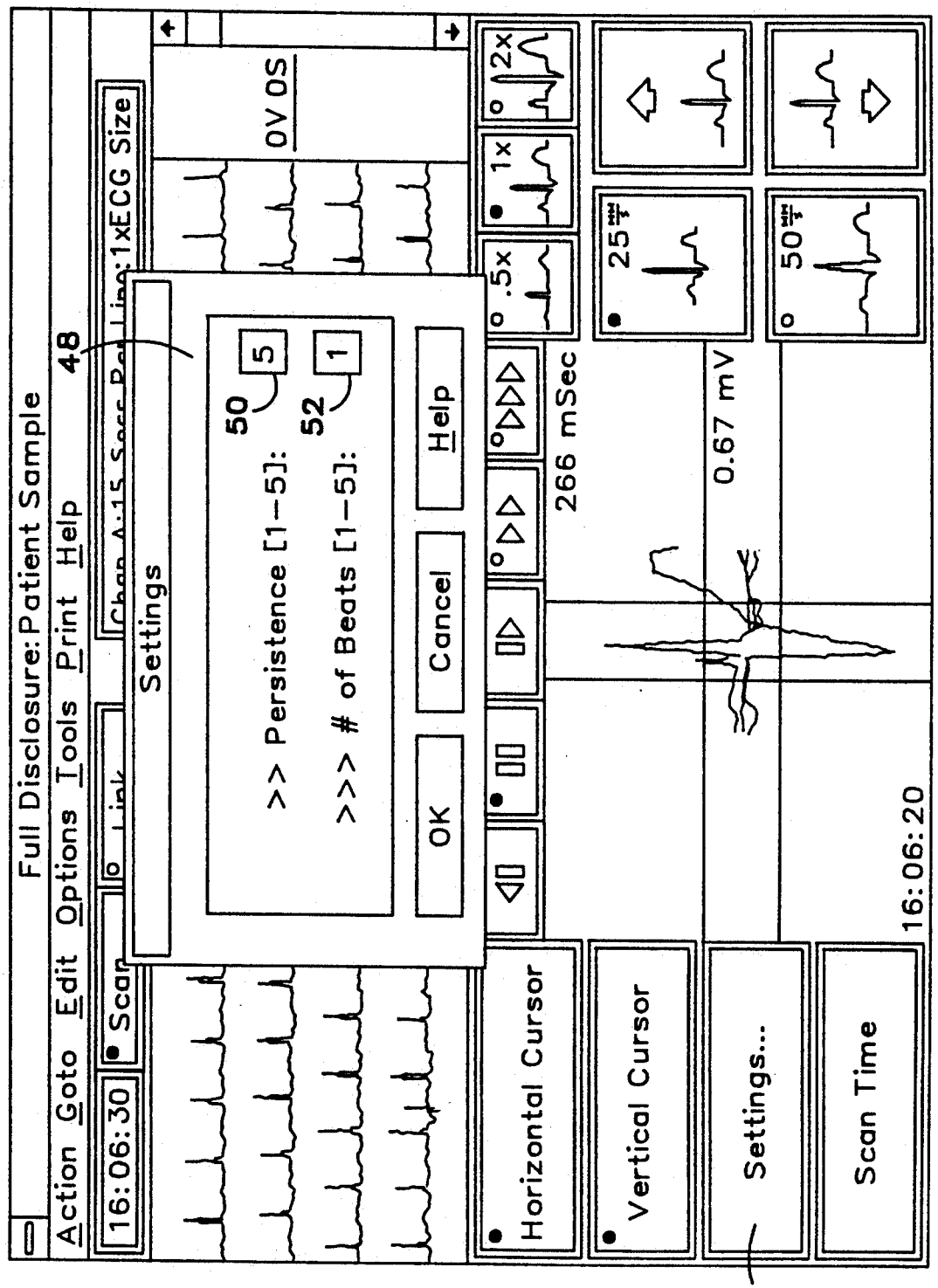
FIG. 2 is a view similar to FIG. 1, with a settings panel opened.
Figure 3:
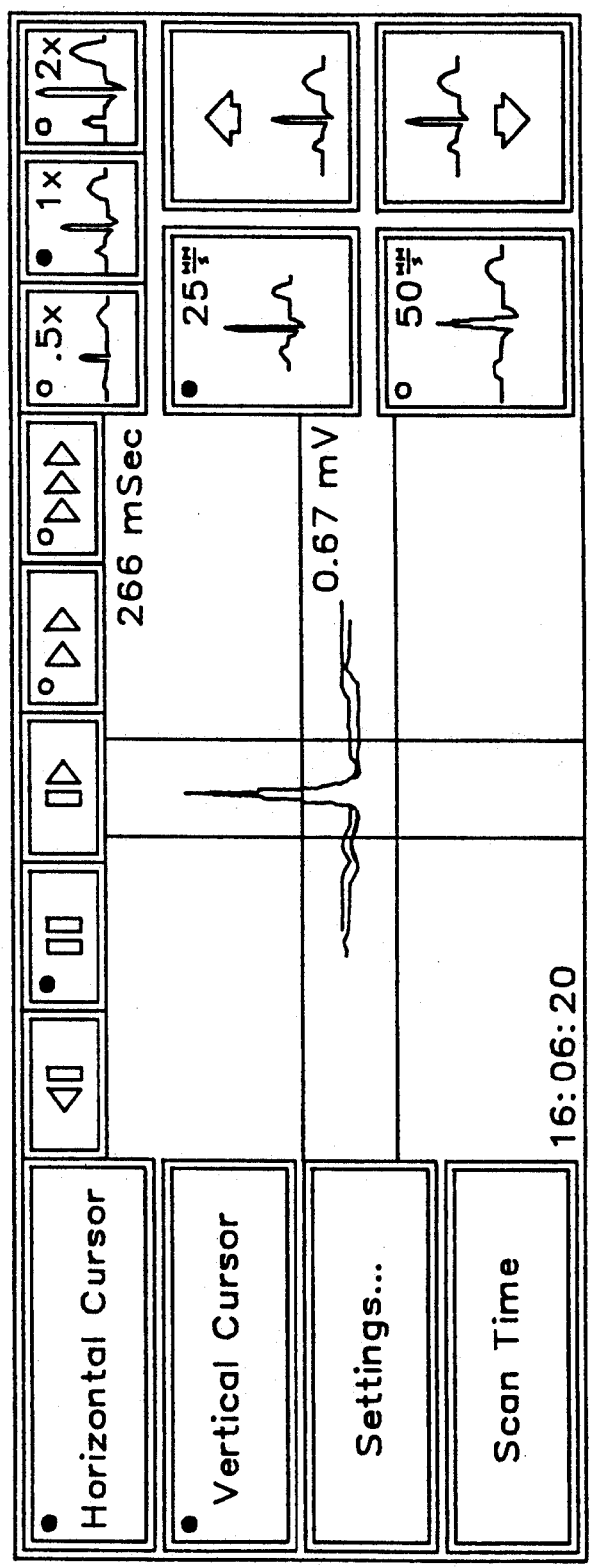
FIG. 3 is a slightly reduced view of the superimposed display of FIG. 1 having three normal heartbeat waveforms displayed thereon.
Figure 4:
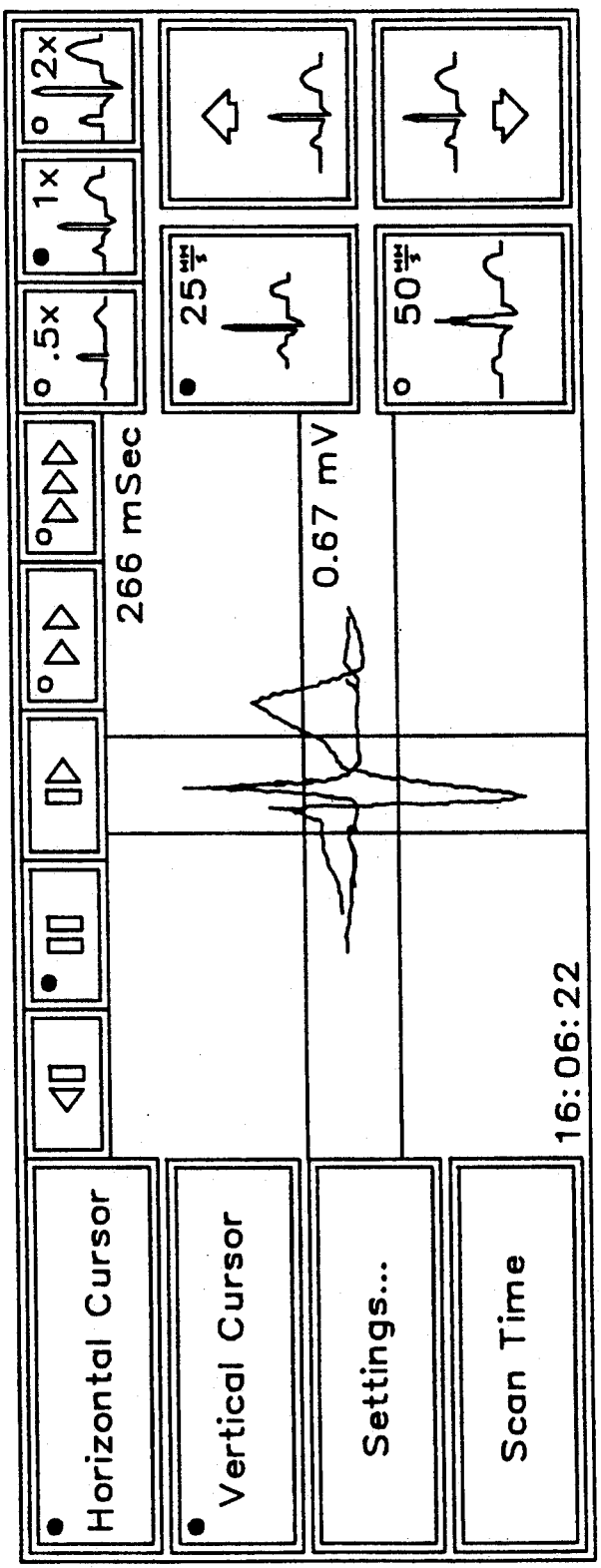
FIG. 4 is a view similar to FIG. 3 having two normal and one abnormal heartbeat waveforms displayed thereon.
Figure 5:
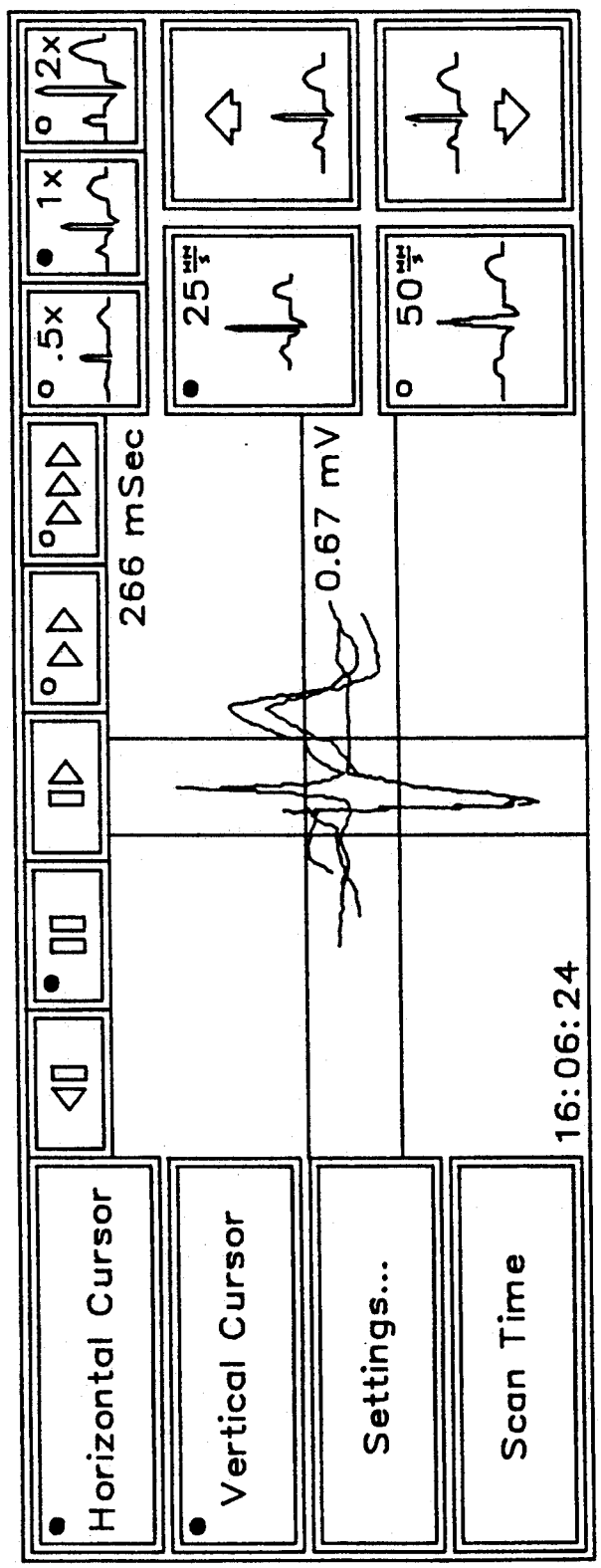
FIG. 5 is a view similar to FIG. 3 having one normal and two abnormal heartbeat waveforms displayed thereon.
Figure 6:
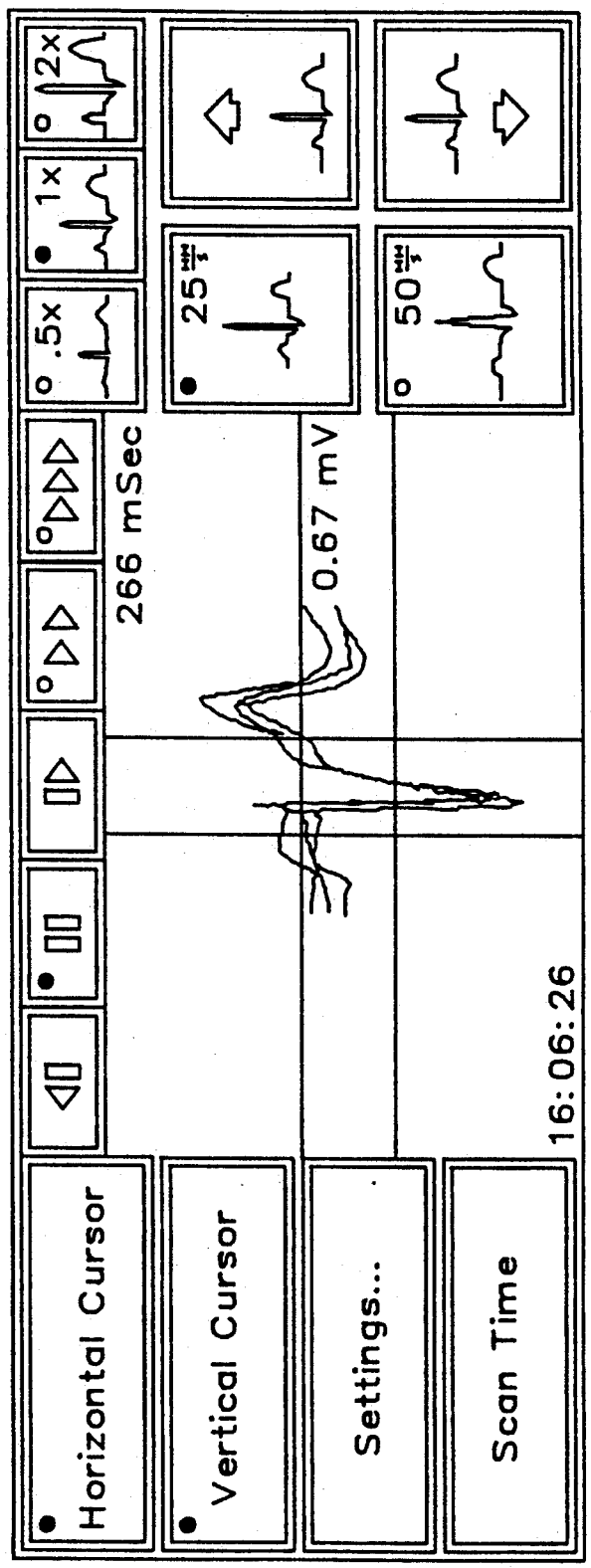
FIG. 6 is a view similar to FIG. 3 having three abnormal heartbeat waveforms displayed thereon.

A settings button 46 causes a panel 48 (in FIG. 2) to appear as shown in FIG. 2 when button 46 is actuated. The panel includes data-entry boxes 50, 52 each of which may receive an integer from one to five for the purpose of controlling the manner in which display 14 scans when any of buttons 38, 40, 42, 44 are actuated. The number in box 50 determines how many beats at one time appear on display 14 when forward button 38 is selected. For example, if the keyboard is used to enter 2 in box 50, beats 24, 26 are simultaneously displayed and in the next refresh cycle beat 24 is removed and beat 28 is added, thereby displaying beats 26, 28. In the next refresh cycle beat 26 is removed and beat 30 added and so forth. The number in box 50 also determines the number of displayed beats when single-beat forward button 40 and single-beat reverse button 42 are actuated.

The number of beats entered in box 52 determines how many beats at a time appear in display 14 when fast-forward button 44 is selected. For example, if a 2 appears in box 52, when button 44 is actuated, beats 24, 26 appear superimposed on display screen 14. During the next refresh cycle, beats 24, 26 are removed and beats 28, 30 appear. In the next refresh cycle beats 28, 30 are removed and beats 32, 34 appear, and so forth. After the keyboard is used to enter the desired numbers in boxes 50, 52, the mouse is used to position the cursor (not shown) over the OK button on panel 48 which closes the panel.

Turning now to FIGS. 3-6, consideration will be given to the manner in which display 14 permits a user to select persistence in box 50 to visually detect a run of abnormal beats of any length which is greater than or equal to the persistence setting. For example, with the value in box 50 set to 3, three superimposed beats are displayed at a time as in FIG. 3. For consecutive normal heartbeats, display 14 appears in FIG. 3 for consecutive refresh cycles of CRT screen 10. If the user encounters a single isolated ectopic beat in a string of normal beats, the user sees the display in FIG. 4 for three cycles. If any two of three consecutive beats are abnormal, the user sees a display as in FIG. 5 for two cycles. If three consecutive beats are abnormal, the user sees a display as in FIG. 6 where only abnormal complexes are displayed for one cycle. If an isolated consecutive run of 3 ectopic heartbeats is encountered in a series of many normal beats, a user sees many cycles of FIG. 3, followed by one cycle of FIG. 4, followed by one cycle of FIG. 5, one cycle of FIG. 6, one cycle of FIG. 5, one cycle of FIG. 4 and many cycles of FIG. 3 again. In the case of a pair of adjacent ectopic heartbeats in a series of many normal beats, the sequence is as follows: many cycles of FIG. 3, one cycle of FIG. 4, one cycle of FIG. 5, one cycle of FIG. 4, and many cycles of FIG. 3.

The user can therefore select a persistence setting to visually detect a run of any length which is equal to or greater than the persistence setting.

Figure 7:
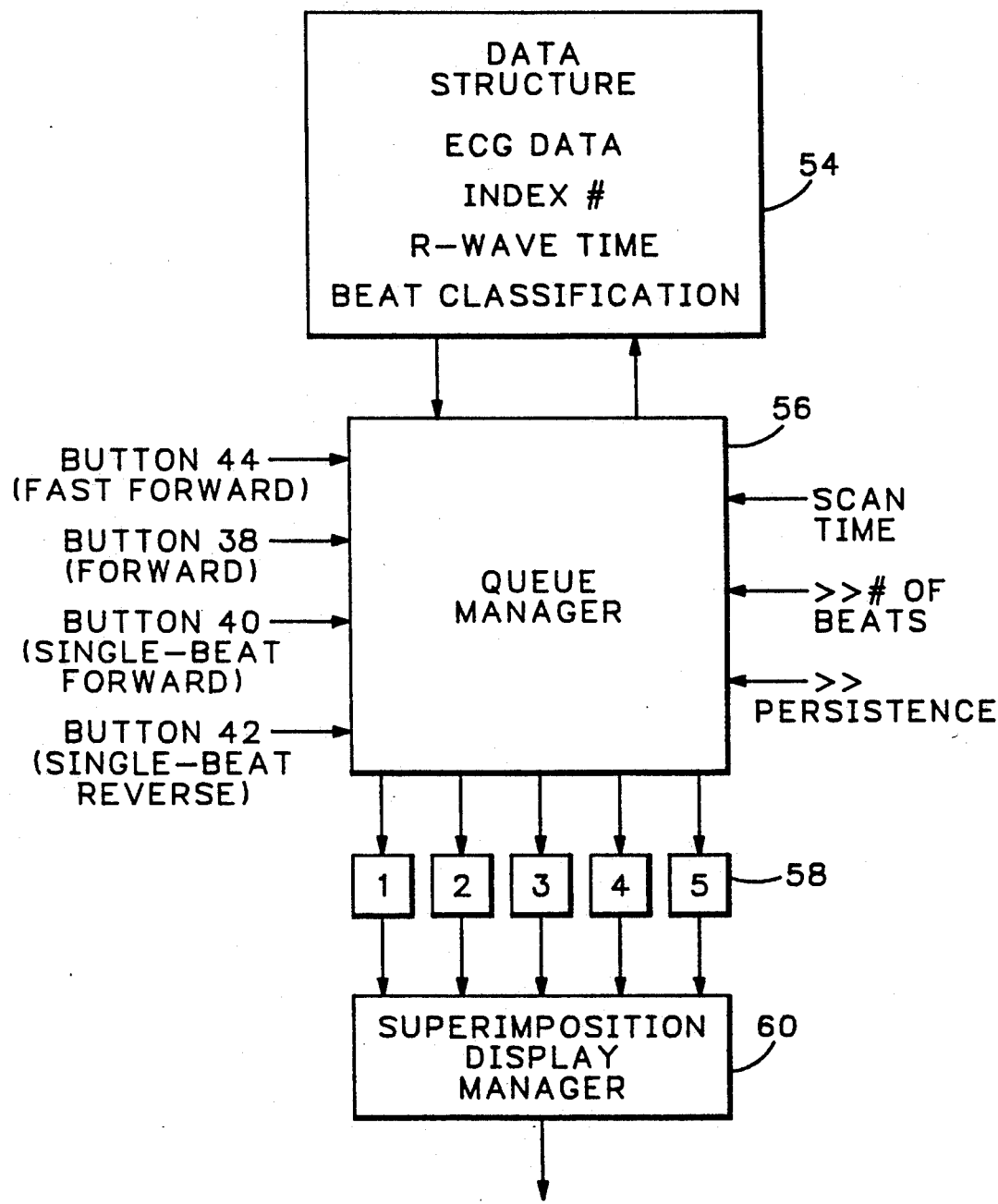
FIG. 7 is a diagram depicting operation of a computer program which in part implements the present embodiment of the invention.

Turning now to FIG. 7, illustrated therein is a chart which depicts operation of a program used to control the computer in the present embodiment of the invention. The program was written for use with Windows 3.0 TM supplied by Microsoft Corporation, using the developer's tool provided for use in writing programs for use with the Windows 3.0 TM graphical user interface.

In the chart of FIG. 7, box 54 represents a data structure which includes the continuous ECG waveform, in digital form, for the entire period monitored as it is received from the Holter monitor. The Holter monitor is of known type which assigns each heartbeat waveform in the ECG data an index number commencing with 1 and increasing by sequential integers. The Holter monitor also assigns a time in hours, minutes, seconds and milliseconds, corresponding to the time of day, to each R-wave in each heartbeat wave form. Finally, the Holter monitor includes a processor which performs limited processing on each heartbeat waveform and assigns a classification, such as ventricular ectopic beat, pace beat, dominant beat, artifact, unknown, etc. When Holter monitoring is complete, the data therein is transferred in a known manner to the computer which controls the display on screen 10 of the CRT. It is this data which is contained in the data structure represented by box 54.

Box 56 represents an object which is identified as a Queue Manager. The Queue Manager receives messages from the Scan Time button (in FIGS. 1 and 2), from buttons 38, 40, 41, 42, 44 and from boxes 50, 52 on panel 48 in FIG. 2. As indicated by the arrow pointing from box 56 to box 54, Queue Manager 56 uses Scan Time information to point to the heartbeat waveform nearest to the selected time in the ECG data. Queue Manager 56 selects one or several consecutive heartbeats from the data structure depending upon which of buttons 38, 40, 42, 44 is actuated and on the numbers appearing in boxes 50, 52 to effect operation as described above. Queue Manager 56 is synchronized in a known manner with the circuitry (not shown) which controls the refresh rate of CRT screen 10.

Queue Manager 56 provides a single heartbeat to one or more of 5 beat-bin objects indicated generally at 58 between refresh cycles so as to display beats superimposed in accordance with the settings of the buttons, the scan time and the numbers in boxes 50, 52.

A Superimposition Display manager is an Object represented by box 60. Display Manager 60 likewise is synchronized with the refresh cycle of CRT screen 10 which functions in a known manner to display the waveforms in heartbeat bins 58 superimposed over one another and aligned on their R-waves. The superimposition display manager cooperates with the video circuitry in a known manner to provide such a display.

Figure 8:
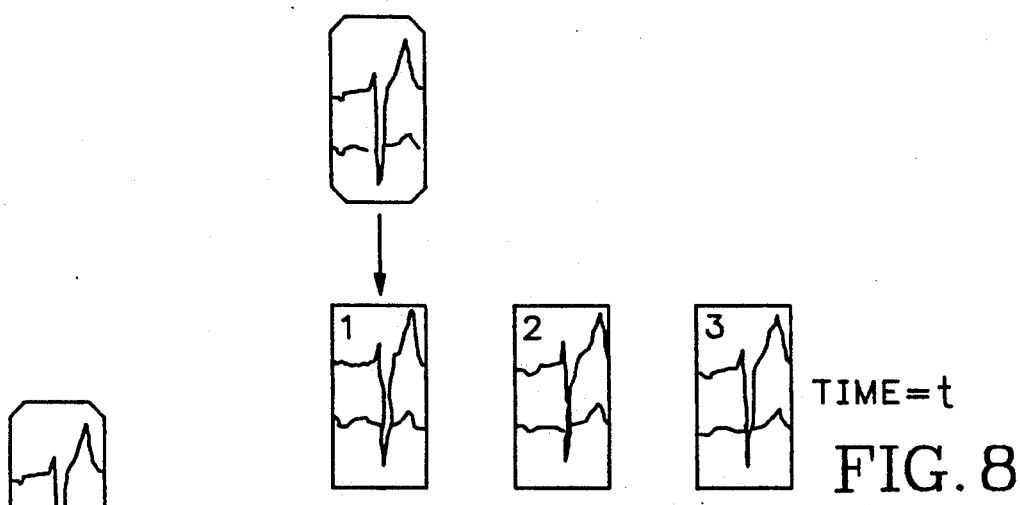
FIGS. 8-11 illustrate operation of the computer program depicted in FIG. 7.
Figure 9:
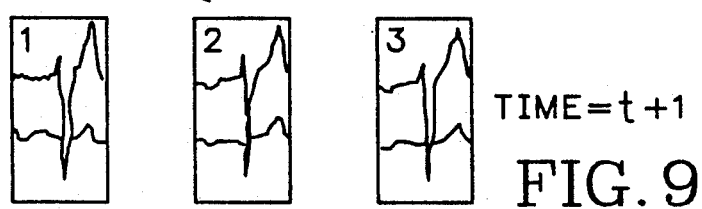
Figure 10:
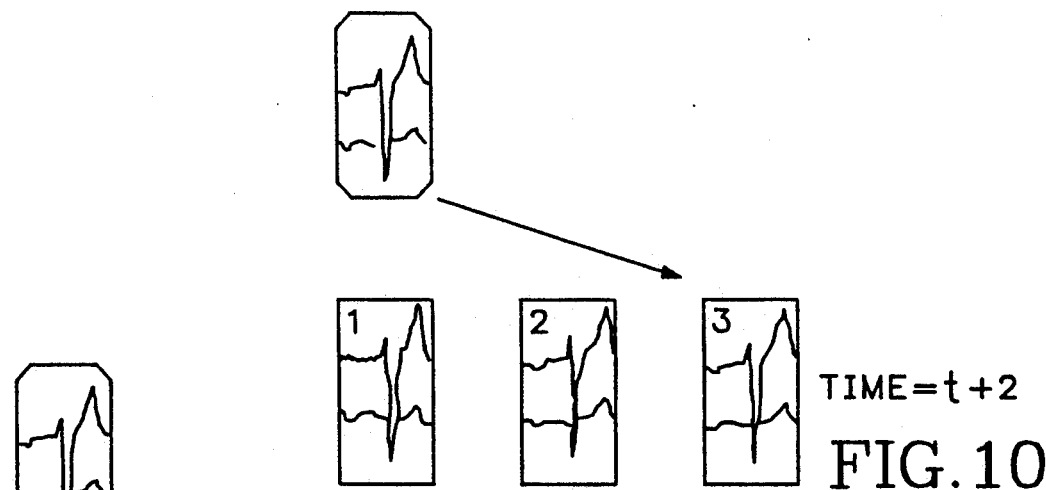
Figure 11:
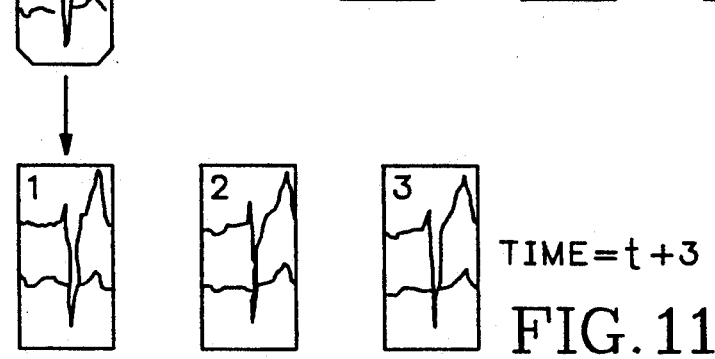
Figure 12:
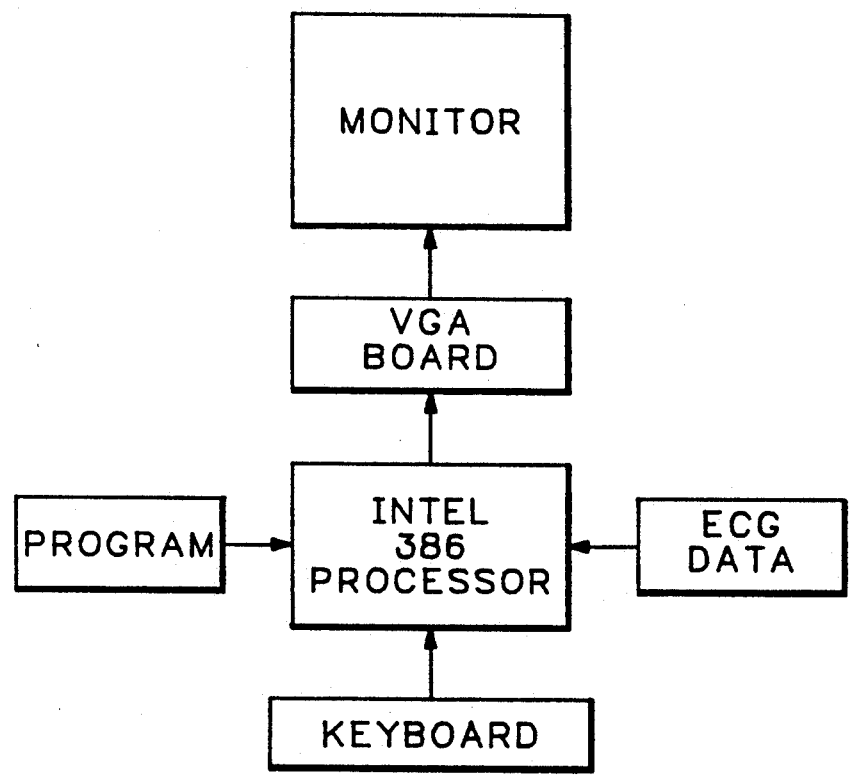
FIG. 12 is a block diagram illustrating a computer system which can be used to carry out the method of the present invention.

By way of example, attention is directed to FIGS. 8-11 which illustrate the contents of the first three beat bins 58 when box 50 in FIG. 2 contains the numeral 3 and when forward button 38 is selected. Because two leads are connected to the patient, two ECG waveforms are simultaneously detected and stored as indicated by the dual waveforms in each beat bin in FIG. 11. In the present mode of operation, however, only heartbeats from a selected one of the ECG waveforms is written to display 14. The following description thus refers only to a single heartbeat being placed in each bin. In FIG. 8, a new beat is provided by Queue Manager 56 from data structure 54 to beat bin 1 with the old beat contained in the bin being overwritten by the new beat. Next, screen 10 refreshes in response to the Superimposition Display Manager in box 60 causing the contents of bin 1-3 to be appear superimposed over one another on display 14. Prior to the next screen refresh cycle, a new beat is placed in bin 2 as indicated in FIG. 9 and then during the next cycle the previously displayed beats in bin 1, 3 are again displayed with the new beat in bin 2. Similarly, prior to the next refresh cycle a new beat is written into bin 3 in FIG. 10 and the previously displayed beats in bins 1,2 are then displayed with the new beat in bin 3 during the next refresh cycle. Finally, the beat which was placed into bin 1 in FIG. 8 is overwritten in FIG. 11 and during the next refresh cycle the previously displayed beats in bins 2, 3 are then displayed with the new beat in bin 1.

The behavior described in FIGS. 8-11 is similar when single-beat forward button 40 is used to scan the ECG heartbeats except that many refresh cycles may pass before a new beat is written, in response to an operator's actuation of button 40, into one of the beat-bins.

The operation is similar when single-beat reverse button 42 is actuated except that the Queue Manager begins drawing additional sequential beats in reverse chronological order from data structure 54.

When fast-forward button 44 is actuated, the Queue Manager pulls N sequential beats at a time from data structure 54 where N is the number appearing in box 52 in FIG. 2. When in fast-forward mode, all three boxes are simultaneously overwritten with new beats between each refresh cycle, when N=3.

As noted above, the numbers in boxes 50, 52 can range by integers between 1 and 5. The above example holds generally true for selected values other than 3. For example, when 4 is selected, 4 beat-bins are utilized; when 5 is selected, 5 beat-bins are utilized.

It should be appreciated that a computer programmer having ordinary skill in the art of programming in the C language in the context of screen display objects such as the buttons and waveforms illustrated in FIGS. 1 and 2 could implement a computer program based on the chart of FIGS. 7, the associated description thereof and the other figures and related description.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

1. A method for displaying superimposed heartbeat waveforms contained in stored ECG data comprising the steps of:
    defining a data window having a length substantially equal to a predetermined number of successive heartbeats contained in the stored ECG data;
    advancing the window across the data in one heartbeat increments so that each window position contains the predetermined number of heartbeats;
    displaying the heartbeats contained in the window superimposed over one another; and
    varying the predetermined number of successive heartbeats contained in the window.

2. The method of claim 1 wherein the step of advancing the window across the data in one heartbeat increments so that each window position contains the predetermined number of heartbeats further comprises the step of automatically advancing the window upon each occurrence of a predetermined time interval.

3. The method of claim 2 wherein said heartbeats are displayed on a display screen and wherein the step of displaying the heartbeats contained in the window comprises the step of writing the heartbeats to a display screen.

4. The method of claim 1 wherein the step of advancing the window across the data in one heartbeat increments further comprises the step of advancing the window responsive to an operator signal.

5. The method of claim 1 wherein the heartbeat waveforms contained in the stored ECG data are stored in chronological order and wherein the step of advancing the window across the data in one heartbeat increments comprises the step of advancing the window in the direction of increasing time.

6. The method of claim 1 wherein the heartbeat waveforms contained in the stored ECG data are stored in chronological order and wherein the step of advancing the window across the data in one heartbeat increments comprises the step of advancing the window in the direction of decreasing time.

* * * * *